United States Patent
Zhang et al.

(10) Patent No.: US 9,962,688 B2
(45) Date of Patent: May 8, 2018

(54) METHOD FOR SYNTHESIZING MOLECULAR SIEVE SSZ-13

(71) Applicant: BEIJING UNIVERSITY OF CHEMICAL TECHNOLOGY, Beijing (CN)

(72) Inventors: Runduo Zhang, Beijing (CN); Biaohua Chen, Beijing (CN); Ruinian Xu, Beijing (CN)

(73) Assignee: BEIJING UNIVERSITY OF CHEMICAL TECHNOLOGY, Beijing (CN)

(*) Notice: Subject to any disclaimer, the term of this patent is extended or adjusted under 35 U.S.C. 154(b) by 5 days.

(21) Appl. No.: 15/316,119

(22) PCT Filed: Apr. 10, 2014

(86) PCT No.: PCT/CN2014/075043
§ 371 (c)(1),
(2) Date: Dec. 2, 2016

(87) PCT Pub. No.: WO2015/081648
PCT Pub. Date: Jun. 11, 2015

(65) Prior Publication Data
US 2017/0113210 A1    Apr. 27, 2017

(30) Foreign Application Priority Data
Dec. 4, 2013 (CN) .......... 2013 1 0645906

(51) Int. Cl.
*B01J 29/70* (2006.01)
*C01B 39/48* (2006.01)
(Continued)

(52) U.S. Cl.
CPC .............. *B01J 29/70* (2013.01); *B01J 20/18* (2013.01); *B01J 20/3071* (2013.01);
(Continued)

(58) Field of Classification Search
CPC .......... C01B 39/48; B01J 29/723; B01J 20/18
See application file for complete search history.

(56) References Cited

U.S. PATENT DOCUMENTS

| 4,544,538 A | 10/1985 | Zones |
| 4,683,214 A | 7/1987 | Angevine et al. |

(Continued)

FOREIGN PATENT DOCUMENTS

| CN | 101573293 A | 11/2009 |
| CN | 103601211 A | 2/2014 |
| GB | 2079735 A | 1/1982 |

OTHER PUBLICATIONS

Das et al.; "Studies of the synthesis of ETS-10 II. Use of organic templates"; Microporous Materials; vol. 5; Feb. 1996; p. 401-410.
(Continued)

*Primary Examiner* — David M Brunsman
(74) *Attorney, Agent, or Firm* — Baker & Hostetler LLP (57) ABSTRACT

A method for synthesizing a crystalline molecular sieve SSZ-13, characterized in that the method comprises bringing the following raw materials into contact in water under a crystallization condition: at least one tetravalent silicon source, at least one trivalent aluminum source, at least one alkali metal compound, choline cations and/or SSZ-13 seed crystals, and hydroxide ions. The method avoids using benzyl trimethyl quaternary ammonium ions ($BzTMA^+$) or N,N,N-trimethyl-1-amantadine cations as structure-directing agents, and obtains high-quality crystal molecular sieve SSZ-13. Due to the use of a low-cost nontoxic structure-directing agent, the method has low production price by employing a low-cost nontoxic template, and can be popularized for application.

2 Claims, 3 Drawing Sheets (51) Int. Cl.
*B01J 20/18* (2006.01)
*B01J 20/30* (2006.01)
*B01J 35/02* (2006.01)
*B01J 37/00* (2006.01)
*B01J 37/06* (2006.01)
*B01J 37/08* (2006.01)
*B01J 37/10* (2006.01)
*C07C 1/20* (2006.01)

(52) U.S. Cl.
CPC ........... *B01J 20/3085* (2013.01); *B01J 35/02* (2013.01); *B01J 37/0018* (2013.01); *B01J 37/06* (2013.01); *B01J 37/082* (2013.01); *B01J 37/10* (2013.01); *C01B 39/48* (2013.01); *C07C 1/20* (2013.01); *C01P 2002/72* (2013.01); *C07C 2529/70* (2013.01)

(56) References Cited

U.S. PATENT DOCUMENTS

| | | | | |
|---|---|---|---|---|
| 9,334,171 | B2* | 5/2016 | Yilmaz | ................. B01J 20/186 |
| 9,643,899 | B2* | 5/2017 | Fickel | .................. B01J 29/7015 |
| 2012/0004485 | A1 | 1/2012 | Jan et al. | |
| 2012/0208691 | A1* | 8/2012 | Bull | ........................ B01J 29/72 |
| | | | | 502/60 |

OTHER PUBLICATIONS

U.S. Appl. No. 60/826,882, filed Sep. 25, 2006, Zones.
U.S. Appl. No. 60/882,010, filed Dec. 27, 2006, Miller.

* cited by examiner

METHOD FOR SYNTHESIZING MOLECULAR SIEVE SSZ-13

CROSS-REFERENCE TO RELATED APPLICATIONS

This is a national stage application in the United States of International Patent Application No. PCT/CN2014/075043, with an international filing date of Apr. 10, 2014, which claims priority to Chinese Patent Application No. 201310645906.4, filed on Dec. 4, 2013, the entire contents of which are incorporated herein by reference.

TECHNICAL FIELD

The present invention belongs to the field of molecular sieves, and particularly provides a method for synthesizing a molecular sieve SSZ-13 at a low cost.

BACKGROUND ART

It is well recognized that, among naturally occurring and synthetic molecular sieves, aluminum silicate molecular sieves have the most important and most effective crystal composition. X-ray diffraction testing shows that most of the aluminum silicate crystals have clear and different crystal structures and ordered open-framework structures. Different types of molecular sieves have different characteristic open-framework crystal structures.

The different types of molecular sieve are defined by International Zeolite Association (IZA) as different structure codes, such as FAU, MFI, BEA and CHA. As is well known, a molecular sieve SSZ-13 has a CHA topological structure and its synthesis method was firstly disclosed in U.S. Pat. No. 4,544,538 on Oct. 1, 1985. In U.S. Pat. No. 4,544,538, under a condition where the organic cation N,N,N-trimethyl-1-amantadine ($TMAA^+$) is used as a structure-directing agent, the molecular sieve SSZ-13 may be synthesized. However, due to the structure-directing agent used is greatly expensive, the synthesis cost of the molecular sieve SSZ-13 is rather high, thereby limiting the application of the molecular sieve SSZ-13 in commercial production. The present invention has provided a method for synthesizing the molecular sieve SSZ-13 without using the expensive $TMAA^+$ as a structure-directing agent.

It is disclosed in the description of U.S. Pat. No. 60/826,882 applied by Zones on Sep. 25, 2006 that Zones developed a method for synthesizing the molecular sieve SSZ-13 using a reduced dose of $TMAA^+$ as a structure-directing agent. The dose of $TMAA^+$ cation may be significantly reduced by adding benzyl quaternary ammonium ions which worked together with $TMAA^+$ cations as the structure-directing agent for reactants. Although such synthesis method effectively reduces the cost, the expensive $TMAA^+$ cation is still used.

It is disclosed in the description of Patent No. 60/882,010 filed by Miller on Dec. 27, 2006 that a method for synthesizing the molecular sieve SSZ-13, wherein N,N,N-trimethyl-1-adamantyl alkyl amine cation is partially replaced with benzyl trimethyl quaternary ammonium ion ($BzTMA^+$) as a structure-directing agent.

Although benzyl trimethyl quaternary ammonium ion has a relatively low price, it cannot become the most suitable structure-directing agent due to its irritation and harmful effect on humans.

In view of these reasons, the present invention is proposed.

SUMMARY OF THE INVENTION

The present application discloses a novel method for synthesizing a crystalline molecular sieve SSZ-13, which can avoid the use of benzyl trimethyl quaternary ammonium ion ($BzTMA^+$) or N,N,N-trimethyl-1-amantadine cation as structure-directing agent and finally obtain high-quality crystalline molecular sieve SSZ-13.

In order to achieve the above objects, the present invention adopts the following technical solutions:

A method for synthesizing a crystalline molecular sieve SSZ-13, comprising bringing the following raw materials into contact in water under a crystallization condition:
(1) at least one tetravalent silicon source;
(2) at least one trivalent aluminium source;
(3) at least one alkali metal compound;
(4) choline cations and/or SSZ-13 seed crystals; and
(5) hydroxide ions.

Wherein, the tetravalent silicon source includes, but is not limited to, silicon-containing oxides and silicate, preferably, the tetravalent silicon source is silicate, silica sol, tetraethyl orthosilicate, deposited silicon dioxide or clay, and more preferably silica sol.

Wherein, the trivalent aluminium source is trivalent aluminum oxide or aluminate, and preferably the trivalent aluminium source is sodium metaaluminate, aluminium oxide or aluminium hydroxide.

Wherein, the alkali metal compound is sodium-containing compound, preferably sodium hydroxide or sodium chloride, and more preferably sodium hydroxide.

Wherein, the choline cation is choline hydroxide or choline chloride, and preferably choline chloride.

Wherein, the SSZ-13 seed crystal is a SSZ-13 molecular sieve synthesized by using the choline cation as a structure-directing agent (e.g. those prepared according to the present invention).

In the preparation method according to the present invention, the molar ratio of water to the tetravalent silicon source ranges from 3:1 to 15:1.

The molar ratio of the tetravalent silicon source to the trivalent aluminium source (i.e. the ratio of silicon to aluminum) is greater than 3, and preferably 50 or above.

In the method according to the present invention, when a structure-directing agent is used, the molar ratios of individual raw material are:
tetravalent silicon source/trivalent aluminium source 10-60;
alkali metal compound/tetravalent silicon source 0.33-0.47;
choline cations/tetravalent silicon source 0.05-0.1; and
hydroxide ions/tetravalent silicon source 0.3-0.6.

When a structure-directing agent is not used, the molar ratios of individual raw material are:
tetravalent silicon source/trivalent aluminium source 10-60;
alkali metal compound/tetravalent silicon source 0.33-0.47;
hydroxide ions/tetravalent silicon source 0.3-0.6; and
the SSZ-13 seed crystal is 1%-10% of the tetravalent silicon source by mass.

When the choline cation and the SSZ-13 seed crystal are simultaneously used for synthesizing the crystalline molecular sieve SSZ-13, the mass ratio of choline cation to the SSZ-13 seed crystal is 2-3.

In the method according to the present invention, after the end of feeding, the reaction mixture is heated for crystallization, wherein the reaction temperature is maintained at 100-200° C.; the crystallization process lasts for at least 4 days; and the product crystals after water-washing are dried at 90-150° C. for 8-12 hours, and then calcined in a muffle furnace at 500-600° C. for 6-10 hours to give crystals of the molecular sieve SSZ-13. Preferably, the reaction temperature is maintained at 140° C.; the crystallization process lasts for 5-35 days; the product crystals after water-washing are dried at 120° C. for 10-11 hours, and then calcined in a muffle furnace at 550° C. for 8 hours to give crystals of the molecular sieve SSZ-13.

The technical solution according to the present invention will be further described in detail below.

The method for synthesizing a crystalline molecular sieve SSZ-13 according to the present invention specifically illustrate the following three technical solutions to synthesize the crystalline molecular sieve SSZ-13 under the conditions: using the choline cation alone as the structure-directing agent; adding the molecular sieve SSZ-13 seed crystal alone without the addition of structure-directing agent; and using the choline cation and the molecular sieve SSZ-13 seed crystal in combination.

One of the technical solutions according to the present invention provides a method for the synthesis of the molecular sieve SSZ-13 using choline chloride as a structure-directing agent (SDA) which has a lower cost compared with benzyl trimethyl quaternary ammonium ion (BzTMA$^+$) and hardly has any toxicity or irritation.

The specific process is described as follows:

a) preparing the reaction mixture:
  wherein, the reaction mixture comprises: (1) at least one tetravalent silicon source; (2) at least one trivalent aluminium source; (3) at least one alkali metal compound; (4) choline cations as the only structure-directing agent (SDA); (5) a large number of hydroxide ions creating a strong alkali environment; and (6) water used for promoting the formation of the precursor of sol-gel from the raw mixture; and b) during the process of heating for crystallization, the precursor mixture is crystallized for sufficient time to form a aluminium-silicon molecular sieve SSZ-13 with a microporous structure.

In order to optimize the entire synthesis method, the inventors, based on a number of experiments and studies, make the following preferred limitations on molar ratios of individual raw material:
  tetravalent silicon source/trivalent aluminium source 10-60;
  alkali metal compound/tetravalent silicon source 0.33-0.47;
  choline cations/tetravalent silicon source 0.05-0.1; and
  hydroxide ions/tetravalent silicon source 0.3-0.6.
  Preferably,
  tetravalent silicon source/trivalent aluminium source 20-40;
  alkali metal compound/tetravalent silicon source 0.4-0.47;
  choline cations/tetravalent silicon source 0.08-0.1; and
  hydroxide ions/tetravalent silicon source 0.4-0.6.

Another technical solution according to the present invention provides a method for synthesizing crystalline molecular sieve SSZ-13 without the use of a structure-directing agent (SDA), which is described as follows:

a) preparing the reaction mixture:
  wherein, the reaction mixture comprises: (1) at least one tetravalent silicon source; (2) at least one trivalent aluminium source; (3) at least one alkali metal compound; (4) a seed crystal sufficient for the formation of the molecular sieve SSZ-13; (5) a large number of hydroxide ions creating a strong alkali environment; and (6) water used for promoting the formation of the precursor of sol-gel from the raw mixture; and b) during the process of heating for crystallization, the precursor mixture is crystallized for sufficient time to form the abovementioned crystalline molecular sieve SSZ-13 with a microporous structure.

In order to optimize the entire synthesis method, the inventors, based on a number of experiments and studies, make the following preferred limitations on molar ratios of individual raw material:
  tetravalent silicon source/trivalent aluminium source 10-60;
  alkali metal compound/tetravalent silicon source 0.33-0.47;
  hydroxide ions/tetravalent silicon source 0.3-0.6; and
  the SSZ-13 seed crystal is 1%-10% of the tetravalent silicon source by mass.
  Preferably,
  tetravalent silicon source/trivalent aluminium source 20-40;
  alkali metal compound/tetravalent silicon source 0.4-0.47;
  hydroxide ions/tetravalent silicon source 0.4-0.6; and
  the SSZ-13 seed crystal is 5%-8% of the tetravalent silicon source by mass.

In addition, the present invention further provides a method for synthesizing the crystalline molecular sieve SSZ-13, wherein choline cations and seed crystals of the molecular sieve SSZ-13 are used in combination as the material (4). When choline cations and seed crystals are used simultaneously for synthesizing the crystalline molecular sieve SSZ-13, the mass ratio of the choline cations to the SSZ-13 seed crystals is 2-3.

The method according to the present invention can produce a synthetic microporous molecular sieve. A small pore microporous molecular sieve is defined as a molecular sieve with an open-pore structure smaller than 5 Å, which is generally considered as a molecular sieve with a maximum open-pore no greater than an eight-membered ring. Such an extremely small pore diameter makes the molecular sieve exhibit stronger hydrothermal stability. This property makes microporous molecular sieves have more advantages in applications compared with molecular sieves with a common pore diameter.

The microporous molecular sieve SSZ-13 involved in the present invention is an aluminum silicate molecular sieve. The SSZ-13 according to the present invention is obtained by adjusting the molar ratio of tetravalent silicon source and trivalent aluminium source, i.e. controlling the molar ratio of silicon to aluminum to be from 3:1 to 50:1; and different ratios of silicon to aluminum may be obtained by changing the relative ratios of reactants. High ratio of silicon to aluminum may also be achieved by post-processing the molecular sieve, for example by dealuminzation or by adding silicon to increase the ratio of silicon to aluminum. Specific operations are known to those skilled in the art, and thus they are not defined specifically in the present invention.

Amounts of individual components in the precursor mixture according to the present invention may be adjusted depending on the desired molecular sieve SSZ-13. Under the adopted synthesis condition, the present invention provides a relative high ratio of silicon to aluminum; the molar ratio of the tetravalent silicon source to the trivalent aluminium source is greater than 3:1; and the ratio may be up to 50:1 or higher. When commercial silicon or aluminum sources are used as reaction materials, some other trivalent or tetravalent ingredients contained therein such as germanium dioxide and ferric oxide may also be brought into the mixture.

The most typical silicon sources include colloided silica, silicate, hydrated silica gel, tetraethyl orthosilicate, deposited silicon dioxide and clay. The optimum solution is to use silica sol (such as AS-40 silica sol) as the silicon source: it is found that using the hydrated colloided silica as a reactant may relatively reduce the reaction time and increase the crystallization volume through repeated experiments. Thus, most preferably, commercially available AS-40 silica sol is used as the silicon source.

In the technical solution according to the present invention, typical aluminum sources include sodium metaaluminate, aluminium oxide, aluminium hydroxide or other aluminum compounds.

The alkali metal compound (e.g. alkali metal ion-containing salts and alkali metal ion-containing alkalis) according to the present invention especially sodium ion is often used to balance the negative charges in the molecular sieve framework structure. Generally, the negative charges are produced by the replacement of a tetravalent atom in the structure with a trivalent atom. In aluminum silicate molecular sieve, the trivalent atom is an aluminum atom and the tetravalent atom is a silicon atom. When the silicon atom in the structure is replaced with an aluminum atom, each aluminum atom needs one positron to balance the charges. Thus, theoretically, the number of alkali metal ions should be the same as that of aluminum atoms. In particular experiments, in order to significantly reduce the reaction time, the number of sodium ions should be more than the theoretical number. The reaction mixture contains one or more alkali metals.

The present invention provides a new structure-directing agent for the synthesis of the molecular sieve SSZ-13, namely choline cation, which is also named as hydroxyethyl trimethyl ammonium cation. Choline has been widely used in animal husbandry, and choline chloride is one kind of vitamin B. However, the choline cation has not been used as the structure-directing agent yet. In the specific operation of the present invention, choline chloride is preferably used as the only structure-directing agent.

In addition to the above raw materials, the present invention further needs hydroxide ions to create an alkali environment to prepare for the preparation of the molecular sieve. In the present invention, the alkali environment is necessary for the synthesis of the molecular sieve SSZ-13 and the amount of the hydroxide ions should be sufficient for the formation of the necessary alkali environment. In the present invention, the molar ratio of the hydroxide ions to the tetravalent silicon source is preferably 0.4-0.6.

In order to optimize the entire synthesis method, the inventors, based on a number of experiments and studies, make the preferred limitations on molar ratios of individual raw material:
 tetravalent silicon compound/trivalent aluminium compound 10-60;
 alkali metal sodium/tetravalent silicon compound 0.33-0.47;
 choline cations and/or seed crystals/tetravalent silicon compound 0.05-0.1; and
 hydroxide ions/tetravalent silicon compound 0.3-0.6.
Wherein, more preferably,
 tetravalent silicon source/trivalent aluminium source 20-40;
 alkali metal compound/tetravalent silicon source 0.4-0.47;
 choline cations/tetravalent silicon source 0.08-0.1; and
 hydroxide ions/tetravalent silicon source 0.4-0.6.

After getting the materials ready according to the above ratios, the reaction mixture is maintained under a reaction temperature environment until the crystal of the molecular sieve SSZ-13 is formed. In the present invention, the reaction temperature is maintained at 100-200° C. and preferably maintained at a constant temperature of 140° C. during the hydrothermal synthesis step. The crystallization process needs to be performed for at least 4 days and also may be performed for 5 days to 35 days. In order to make the reaction mixture react under a pressure generated spontaneously, the hydrothermal synthesis reaction is generally performed in a static pressure reactor.

The molecular sieve SSZ-13 crystals are formed after the required reaction time, and then the solid products are separated through standard separation technologies (such as filtration). The product crystals after water-washing are dried at 90-150° C. for 8-12 hours to give the synthesized molecular sieve SSZ-13 crystals.

In the hydrothermal synthesis step, SSZ-13 molecular sieve may spontaneous nucleate from the reaction mixture. Addition of seed crystals of the molecular sieve SSZ-13 into the reaction mixture may not only accelerate the crystallization process but also reduce the formation of other aluminosilicate byproducts. When the molecular sieve SSZ-13 crystals are added into the reaction mixture, the amount required for the structure-directing agent may also be greatly reduced, even the structure-directing agent may not be used, however, the SSZ-13 may be better synthesized with the addition of some structure-directing agents. When the seed crystals are added alone, the added seed crystals is 1 to 10%, preferably 5-8% by mass of the silicon oxide in the reaction mixture. When choline cations and/or seed crystals are simultaneously used for the synthesis of the crystalline molecular sieve SSZ-13, the mass ratio of choline cations to seed crystals is preferably (2-3):1, the molecular sieve SSZ-13 with higher quality may be obtained within such a range.

The molecular sieve SSZ-13 prepared according to the present invention may be used directly in the MTO (preparation of olefins such as ethylene and propylene from methanol) reaction and may also be prepared into molecular sieve membranes used in the applications of separating carbon dioxide from methane and environmental protection such as the absorption of carbon monoxide and light hydrocarbons. It has been found in the latest studies that the molecular sieve SSZ-13, after subjecting to the ion-exchange with transition metals (Cu, Fe), may exhibit extremely excellent catalytic activity in the reaction in which $NO_x$ is removed by $NH_3$—SCR. In addition, since a low-cost and nontoxic structure-directing agent is used in the present invention, the preparation method according to the present invention also has the advantages such as low production price and easy popularization for application.

BEST MODE OF THE INVENTION

The following examples are described for the purpose of illustrating the present invention rather than limiting the scope of the present invention.

The chemical reagents used in the following examples are commercially available.

Example 1

0.492 g of sodium metaaluminate (aluminum source) and 3.6 g of sodium hydroxide were dissolved in 15.8 g of deionized water and stirred to dissolve completely. 2.3 g of choline chloride was added into the obtained mixture and stirred for 15 minutes to dissolve completely. 18 g of LUDOX-AS-40 silica sol (silicon source) was slowly added dropwise under rapid stirring.

After stirring at room temperature for one hour, the final colloid was divided into two parts (A and B), then A and B were respectively transferred into a stainless steel high-pressure reactor with a polytetrafluoroethylene lining, placed in an oven at 140° C. and kept for 4 days (for A) and 6 days (for B) respectively.

Figure 1:
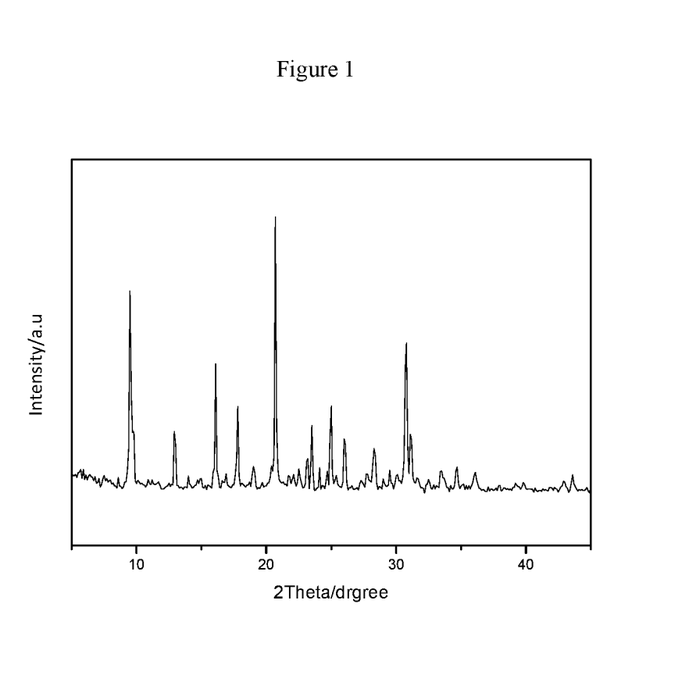
FIG. 1 shows the XRD spectra of the molecular sieve SSZ-13 sample prepared in Example 1(A).
Figure 2:
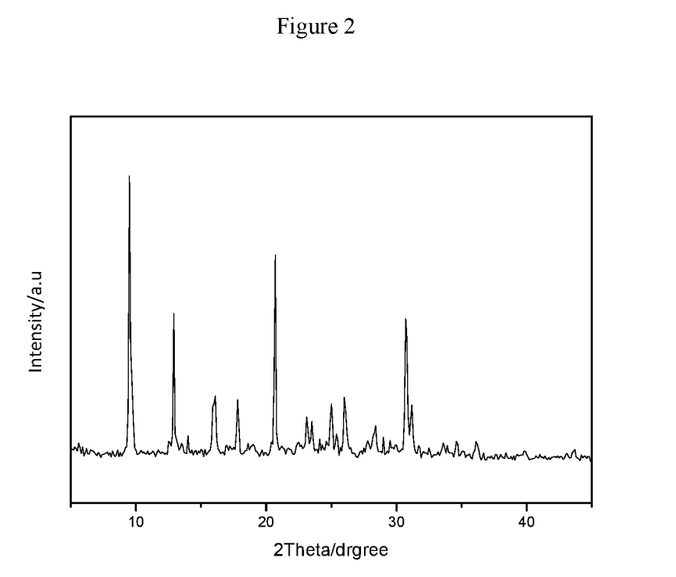
FIG. 2 shows the XRD spectra for the molecular sieve SSZ-13 sample prepared in Example 1(B).

The obtained product was washed with deionized water, collected after filtration, dried in a vacuum oven at 100° C. for 12 hours, and then calcined in a muffle furnace at 550° C. for 8 hours to remove the structure-directing agent so as to give the molecular sieve SSZ-13. Wherein, FIGS. 1 and 2 showed the XRD spectra of the molecular sieve SSZ-13 prepared in the two groups, A and B.

Example 2

0.853 g of sodium metaaluminate (aluminum source) and 3.0 g of sodium hydroxide were dissolved in 15.8 g of deionized water and stirred to dissolve completely. 1.8 g of choline chloride was added into the obtained mixture and stirred for 15 minutes to dissolve completely. 17.25 g of LUDOX-AS-40 colloided silica (silicon source) was slowly added dropwise under rapid stirring.

After stirring at room temperature for one hour, the final colloid was divided into two parts (A and B), then A and B were respectively transferred into a stainless steel high-pressure reactor with a polytetrafluoroethylene lining, placed in an oven at 130° C. (for A) and 150° C. (for B) respectively and kept for 6 days.

Figure 3:
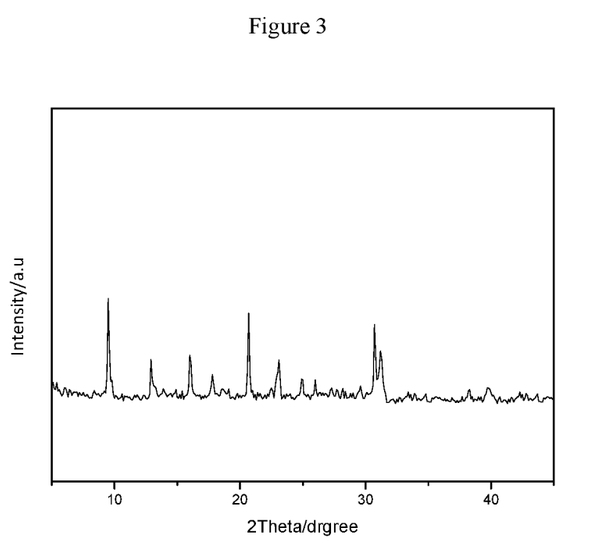
FIG. 3 shows the XRD spectra for the molecular sieve SSZ-13 sample prepared in Example 2(A).
Figure 4:
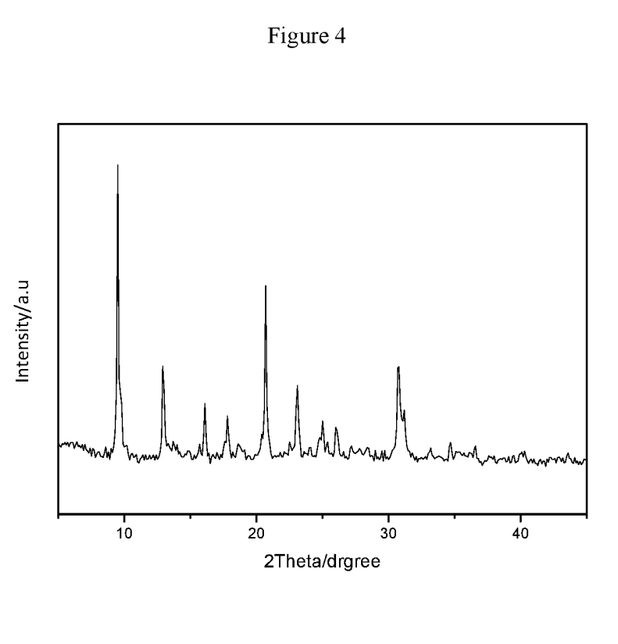
FIG. 4 shows the XRD spectra for the molecular sieve SSZ-13 sample prepared in Example 2(B).

The obtained product was washed with deionized water, collected after filtration, dried in a vacuum oven at 100° C. for 12 hours, and then calcined in a muffle furnace at 550° C. for 8 hours to remove the structure-directing agent so as to give the molecular sieve SSZ-13. Wherein, FIGS. 3 and 4 showed the XRD spectra of the molecular sieve SSZ-13 prepared in the two groups, A and B.

Example 3

0.492 g of sodium metaaluminate (aluminum source) and 3.0 g of sodium hydroxide were dissolved in 15.8 g of deionized water and stirred to dissolve completely. 1.2 g of choline chloride was added into the obtained mixture and it took 15 minutes to mix completely. 0.36 g of SSZ-13 seed crystal was added and it took 5 minutes to mix completely. 18.0 g of LUDOX-AS-40 silica sol (silicon source) was slowly added dropwise under rapid stirring.

After stirring at room temperature for one hour, the mixture was transferred into a stainless steel high-pressure reactor with a polytetrafluoroethylene lining, placed in an oven at 140° C. and kept for 4 days.

Figure 5:
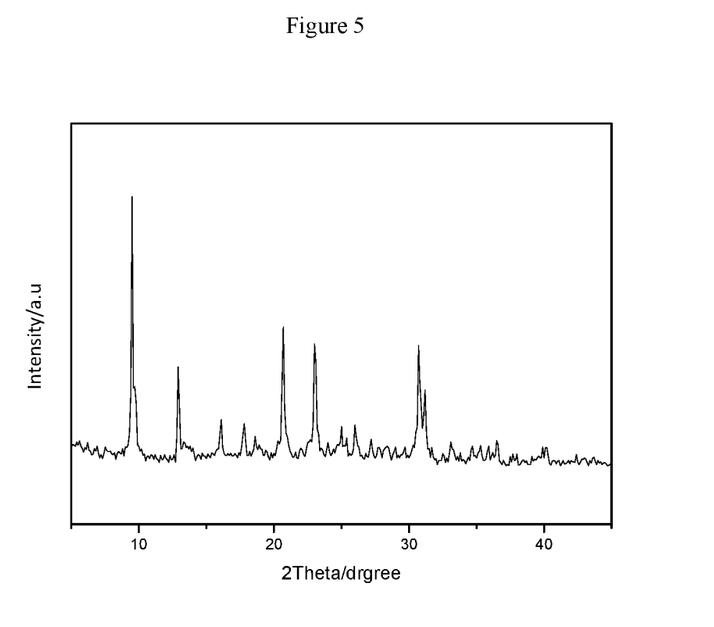
FIG. 5 shows the XRD spectra for the molecular sieve SSZ-13 sample prepared in Example 3.

The obtained product was washed with deionized water, collected after filtration, dried in a vacuum oven at 100° C. for 12 hours, and then calcined in a muffle furnace at 550° C. for 8 hours to remove the structure-directing agent so as to give the molecular sieve SSZ-13. Wherein, FIG. 5 showed the XRD spectra of the molecular sieve SSZ-13.

Example 4

0.492 g of sodium metaaluminate (aluminum source) and 3.0 g of sodium hydroxide were dissolved in 15.8 g of deionized water and stirred to dissolve completely. 0.72 g of SSZ-13 seed crystal was added into the obtained mixture and stirred for 15 minutes to dissolve completely. 18.0 g of LUDOX-AS-40 silica sol (silicon source) was slowly added dropwise under rapid stirring.

After stirring at room temperature for one hour, the mixture was transferred into a stainless steel high-pressure reactor with a polytetrafluoroethylene lining, placed in an oven at 140° C. and kept for 6 days.

Figure 6:
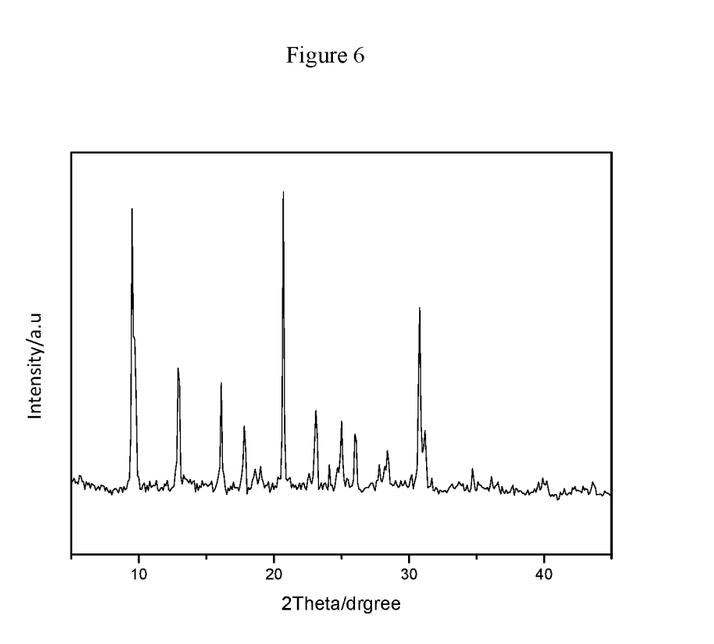
FIG. 6 shows the XRD spectra for the molecular sieve SSZ-13 sample prepared in Example 4.

The obtained product was washed with deionized water, collected after filtration, dried in a vacuum oven at 100° C. for 12 hours, and then calcined in a muffle furnace at 550° C. for 8 hours to remove the structure-directing agent so as to give the molecular sieve SSZ-13. Wherein, FIG. 6 showed the XRD spectra of the molecular sieve SSZ-13.

Example 5

The difference of Example 5 compared with Example 4 merely lied in the specific selection and molar quantity of individual raw material, which were specifically as follows:

tetravalent silicon source/trivalent aluminium source 10;
alkali metal compound/tetravalent silicon source 0.33;
hydroxide ion/tetravalent silicon source 0.33;
$H_2O$/tetravalent silicon source 3; and
seed crystal/tetravalent silicon source (Wt. %) 4.

In this example, the tetravalent silicon source was deposited silicon dioxide, the trivalent aluminium source was pseudo-bohemite, the alkali metal compound was sodium hydroxide, and the hydroxide ion was provided in the form of sodium hydroxide. The XRD spectrum of the molecular sieve SSZ-13 prepared in this example, as compared with FIGS. 1-6, showed characteristic diffraction peaks at the same positions, which confirmed that the preparation method as described in this example obtained the same molecular sieve SSZ-13. The spectrum was not provided here due to the space constraints. Those skilled in the art may predict that using the above-mentioned technical solution can achieve the object of the present invention, obtaining the expected molecular sieve SSZ-13.

Example 6

The difference of Example 6 compared with Example 4 merely lied in the specific selection and molar quantity of individual raw material, which were specifically as follows:

tetravalent silicon source/trivalent aluminium source 60;
alkali metal compound/tetravalent silicon source 0.47;
hydroxide ion/tetravalent silicon source 0.47;
$H_2O/SiO_2$ 11; and
seed crystal/tetravalent silicon source (Wt. %) 10.

In this example, the tetravalent silicon source was tetraethyl orthosilicate, the trivalent aluminium source was sodium metaaluminate, the alkali metal compound was sodium hydroxide, and the hydroxide ion was provided in the form of sodium hydroxide. The XRD spectrum of the molecular sieve SSZ-13 prepared in this example, as compared with FIGS. 1-6, showed characteristic diffraction peaks at the same positions, which confirmed that the preparation method as described in this example obtained the same molecular sieve SSZ-13.

Example 7

The difference of Example 7 compared with Example 1 merely lied in the specific selection and molar quantity of individual raw material, which were specifically as follows:
tetravalent silicon source/trivalent aluminium source 20;
alkali metal compound/tetravalent silicon source 0.4;
hydroxide ion/tetravalent silicon source 0.4;
$H_2O$/tetravalent silicon source 11; and
choline chloride/tetravalent silicon source 0.08.

In this example, the tetravalent silicon source was sodium silicate, the trivalent aluminium source was pseudo-boehmite, the alkali metal compound was sodium hydroxide, and the hydroxide ion was provided in the form of sodium hydroxide. The XRD spectrum of the molecular sieve SSZ-13 prepared in this example, as compared with FIGS. 1-6, showed characteristic diffraction peaks at the same positions, which confirmed that the preparation method as described in this example obtained the same molecular sieve SSZ-13.

Example 8

The difference of Example 8 compared with Example 1 merely lied in the specific selection and molar quantity of individual raw material, which were specifically as follows:
tetravalent silicon source/trivalent aluminium source 40;
alkali metal compound/trivalent aluminium source 2.3;
hydroxide ion/tetravalent silicon source 0.5;
$H_2O$/tetravalent silicon source 5; and
choline hydroxide/tetravalent silicon source 0.1.

In this example, the tetravalent silicon source was silica sol, the trivalent aluminium source was aluminum oxide, the alkali metal compound was sodium chloride, and the hydroxide ion was provided in the form of ammonia water. The XRD spectrum of the molecular sieve SSZ-13 prepared in this example, as compared with FIGS. 1-6, showed characteristic diffraction peaks at the same positions, which confirmed that the preparation method as described in this example obtained the same molecular sieve SSZ-13.

Example 9

The difference of Example 9 compared with Example 3 merely lied in that the mass ratio of choline chloride to SSZ-13 seed crystal was 2:1.

Example 10

The difference of Example 10 compared with Example 3 merely lied in that the mass ratio of choline chloride to SSZ-13 seed crystal was 3:1.

Example 11

The difference of Example 11 compared with Example 3 merely lied in that the mass ratio of choline chloride to SSZ-13 seed crystal was 2.5:1.

Although the present invention has been described in detail through the general descriptions and detailed embodiments above, it is obvious to those skilled in the art to make modifications or improvements based on the present invention. Hence, the modifications or improvements which are made without departing from the spirits of the present invention fall into the protection scope claimed by the present invention.

INDUSTRIAL APPLICABILITY

Disclosed is a novel method for synthesizing a crystalline molecular sieve SSZ-13, the method comprises bringing the following raw materials into contact in water under a crystallization condition: (1) at least one tetravalent silicon source, (2) at least one trivalent aluminium source, (3) at least one alkali metal compound, (4) choline cations and/or SSZ-13 seed crystals, and (5) hydroxide ions. The novel method for synthesizing a crystalline molecular sieve SSZ-13 according to the present invention may avoid the use of benzyl trimethyl quaternary ammonium ion ($BzTMA^+$) or N,N,N-trimethyl-1-amantadine cation as the structure-directing agent, and may finally obtain high-quality crystalline molecular sieve SSZ-13. In view of the use of a low-cost and nontoxic structure-directing agent in the present invention, the preparation method according to the present invention also has the following advantages: a low production price due to the use of a low-cost and nontoxic template agent and easy popularization for application, and thus has strong industrial applicability.

What is claimed is:
1. A method for synthesizing a crystalline molecular sieve SSZ-13, characterized in that, the method comprises bringing the following raw materials into contact in water under a crystallization condition:
(1) at least one tetravalent silicon source;
(2) at least one trivalent aluminium source;
(3) at least one alkali metal compound;
(4) choline cation or a combination of choline cation and SSZ-13 seed crystal; and
(5) hydroxide ion;
wherein the tetravalent silicon source is one or more of silicate, silica sol, tetraethyl orthosilicate, deposited silicon dioxide and clay;
wherein the trivalent aluminium source is sodium metaaluminate, aluminium oxide or aluminium hydroxide;
wherein the alkali compound is sodium hydroxide or sodium chloride;
wherein the choline cation is one or more of choline hydroxide and choline chloride;
wherein the SSZ-13 crystal is a molecular sieve SSZ-13 synthesized by using the choline cation as a structure-directing agent; and wherein the molar ratios of individual raw material are:
tetravalent silicon source/trivalent aluminium source 10-60;
alkali metal compound/tetravalent silicon source 0.33-0.47;
choline cation/tetravalent silicon source 0.05-0.1; and
hydroxide ion/tetravalent silicon source 0.3-0.6.

2. The method according to claim 1, characterized in that, when the choline cation and the SSZ-13 seed crystal are simultaneously used for synthesizing the crystalline molecular sieve SSZ-13, the mass ratio of the choline cation to the SSZ-13 seed crystal is (2-3):1.

* * * * *

UNITED STATES PATENT AND TRADEMARK OFFICE
CERTIFICATE OF CORRECTION

PATENT NO. : 9,962,688 B2  
APPLICATION NO. : 15/316119  
DATED : May 8, 2018  
INVENTOR(S) : Biaohua Chen, Runduo Zhang and Ruinian Xu Page 1 of 1

It is certified that error appears in the above-identified patent and that said Letters Patent is hereby corrected as shown below:

On the Title Page

Inventors; Item (72), delete:
"Runduo ZHANG, Beijing, (CN); Biaohua CHEN, Beijing, (CN); Ruinian XU, Beijing, (CN)"

And insert:
--Biaohua CHEN, Beijing, (CN); Runduo ZHANG, Beijing, (CN); Ruinian XU, Beijing, (CN)--
therefor.

Signed and Sealed this  
Thirty-first Day of July, 2018

Andrei Iancu  
*Director of the United States Patent and Trademark Office*